United States Patent [19]

Pope et al.

[11] 4,410,531
[45] Oct. 18, 1983

[54] ENZYME DERIVED FROM HYALURONIDASE

[75] Inventors: Derek J. Pope, Milton Keynes; Lily Baxendale, Arkley, both of England

[73] Assignee: Biorex Laboratories Limited, England

[21] Appl. No.: 323,990

[22] Filed: Nov. 23, 1981

[30] Foreign Application Priority Data

Dec. 8, 1980 [GB] United Kingdom ............... 8039310

[51] Int. Cl.$^3$ ...................... A61K 37/48; C12N 9/26
[52] U.S. Cl. ..................................... 424/94; 435/201
[58] Field of Search ........................... 435/201; 424/94

[56] References Cited

U.S. PATENT DOCUMENTS 2,488,565 11/1949 Singher et al. .................... 435/201
2,808,362 10/1957 Thompson et al. ................ 435/201
3,728,223 4/1973 Kaneko et al. .................... 435/201

Primary Examiner—Sam Rosen
Attorney, Agent, or Firm—Wenderoth, Lind & Ponack

[57] ABSTRACT

The present invention provides an enzyme which is an odorless, white powder, the pH of a 15000 to 22000 IU/ml. solution of which in carbon dioxide-free physiological saline solution suitable for injection is 4.5 to 7.5, the solution being clear and colorless; a solution of 50000 IU of which in 3 ml. carbon dioxide-free physiological saline solution suitable for injection has a light absorption of not more than 0.60 at 280 nm and of not more than 0.37 at 260 nm; the enzyme having the following percentage amino acid analysis:

| | | |
|---|---|---|
| Asp 11.1 ± 0.4; | Thr 5.8 ± 0.1; | Ser 6.4 ± 0.2; |
| Glu 9.1 ± 0.2; | Pro 5.0 ± 0.5; | Gly 6.6 ± 0.2; |
| Ala 7.4 ± 0.1; | Val 7.9 ± 0.5; | Met 0.8 ± 0.1; |
| Ile 5.2 ± 0.2; | Leu 10.9 ± 0.2; | Tyr 4.4 ± 0.1; |
| Phe 4.5 ± 0.1; | His 2.8 ± 0.2; | Lys 7.6 ± 0.4; |
| Arg 5.6 ± 0.1; | | | said enzyme having a total hexose content of 10.6±0.003%; said enzyme containing not more than 5 μg. albumin per 220000 IU of activity and said enzyme having a molecular weight of 62000 to 70000 determined by gel filtration.

The present invention also provides a process for preparing this enzyme and a dosage unit containing it.

9 Claims, No Drawings

ENZYME DERIVED FROM HYALURONIDASE

BACKGROUND OF THE INVENTION

An enzyme material called hyaluronidase has been known for a number of years, this material catalysing the hydrolysis of hyaluronic acid, the cement substance of tissues.

Many of the hyaluronidase preparations previously available have contained very large amounts of other enzymatically-active materials, in addition to the enzyme which is thought to be actually responsible for the catalysis of the hydrolysis of hyaluronic acid. The heterogeneous nature of hyaluronidase is discussed in a paper by Greiling et al. (Z.physiol.Chem., 340, 243/1965).

Several processes are known for the purification of hyaluronidase (see our British Patent Specifications Nos. 1,060,513 and 1,425,918) and this purified material has been successfully used for the treatment of myocardial infarct and of peripheral circulatory disturbances, including those associated with gangrene.

This extremely useful action of hyaluronidase appears to be due to its "spreading" ability, i.e. its ability to promote rapid diffusion of injected fluids through tissues, as well as its ability to break down aggregations which are responsible for or contribute to the genesis of infarcts and circulatory disturbances. Previously known hyaluronidase preparations were also observed to have a permeability-increasing activity which manifested itself by increasing capillary permeability; we have also observed that known crude hyaluronidase preparations bring about a reduction of the blood pressure. However, such activities are undesirable when hyaluronidase is used to treat myocardial infarcts and peripheral circulatory disturbances.

It has recently been found by Houck and Chang (Inflammation, 3(4), 447–451/1979) that hyaluronidase preparations contain a component which increases the permeability of the microcirculation in skin.

It is an object of the present invention to provide an enzyme preparation which can be obtained from hyaluronidase but which has a greatly reduced content of the component which increases permeability and which also does not bring about a reduction of the blood pressure.

SUMMARY OF THE INVENTION

The enzyme provided by the present invention is an odorless, white powder, the pH of a 15,000 to 22,000 IU/ml. solution of which in carbon dioxide-free physiological saline solution suitable for injection is 4.5 to 7.5, the solution being clear and colorless; a solution of 50,000 IU of which in 3 ml. carbon dioxide-free physiological saline solution suitable for injection has a light absorption of not more than 0.60 at 280 nm and of not more than 0.37 at 260 nm; said enzyme having the following percentage amino acid analysis:

| | | |
|---|---|---|
| Asp 11.1 ± 0.4; | Thr 5.8 ± 0.1; | Ser 6.4 ± 0.2; |
| Glu 9.1 ± 0.2; | Pro 5.0 ± 0.5; | Gly 6.6 ± 0.2; |
| Ala 7.4 ± 0.1; | Val 7.9 ± 0.5; | Met 0.8 ± 0.1; |
| Ile 5.2 ± 0.2; | Leu 10.9 ± 0.2; | Tyr 4.4 ± 0.1; |
| Phe 4.5 ± 0.1; | His 2.8 ± 0.2; | Lys 7.6 ± 0.4; |
| Arg 5.6 ± 0.1; | | | said enzyme have a total hexose content of 10.6±0.003%; said enzyme containing not more than 5 μg. albumin per 220.000 IU of activity and said enzyme having a molecular weight of 62000 to 70000 determined by gel filtration.

The present invention also provides a process for the preparation of the above-described enzyme, wherein crude hyaluronidase is subjected to an ammonium sulphate fractionation by adding ammonium sulphate to a buffered solution of crude hyaluronidase until the degree of ammonium sulphate saturation is about 50%, the precipitate obtained being discarded and the supernatant being adjusted to 70% ammonium sulphate saturation, the precipitate obtained being dialysed and then applied to a cross-linked polyacrylic divinylbenzene resin (for example, the resin available under the Registered Trade Mark "Amberlite" CG 50), whereafter the resin is first washed with 0.1 M phosphate buffer and subsequently eluted with 0.3 M phosphate buffer, the eluate then being subjected to gel filtration through a cross-linked dextran gel which does not contain active carboxymethyl groups (for example, the resin available under the Registered Trade Mark "Sephadex" G-75 or "Sephadex" G-100), followed by isolation of the enzyme.

DETAILED DESCRIPTION OF THE INVENTION

The precipitate obtained by the ammonium sulphate fractionation is preferably separated by centrifuging As indicated above, the precipitate obtained with a degree of ammonium sulphate saturation of 50% is discarded, whereas the precipitate obtained with a degree of ammonium sulphate saturation of 70% is retained and, in this case, the supernatant is discarded. The retained precipitate is, prior to dialysis, preferably dissolved in 0.1 M phosphate buffer (pH 6.0) and also preferably dialysed against the same phosphate buffer.

The 0.1 M phosphate buffer used for washing the resin preferably has a pH of 6.0 and the 0.3 M phosphate buffer used for eluting the resin preferably has a pH of 8.5.

The eluate obtained is preferably dialysed to 70% saturated ammonium sulphate solution and the precipitate obtained may advantageously be separated by centrifuging.

For the subsequent gel filtration step, this precipitate is preferably dissolved in a minimum amount of 0.1 M sodium chloride solution. The filtrate obtained is preferably dialysed against 80% saturated ammonium sulphate solution, the precipitate obtained being recovered, for example, by centrifuging.

Although the elution stage using the cross-linked polyacrylic divinylbenzene may be carried out at about ambient temperature, it is to be understood that all the other stages should be performed at about 4° C. and that when material is stored temporarily during the processing, it should also be kept at about 4° C.

The enzyme according to the present invention is desalted and lyophilised in appropriate containers, which are preferably made of glass. After sealing, the containers are stored at a temperature of 2° to 8° C. in a dry place.

This enzyme is useful as an aid to the survival of myocardial tissue after infarction and is also useful for the treatment of peripheral vascular disease. Administration can be by intravenous or intraarterial injection, a single dosage usually containing 200,000 U of the enzyme.

The following Example is given for the purpose of illustrating the present invention:

EXAMPLE

Stage 1

Ammonium Sulphate Fractionation of Crude Enzyme 125 g. Crude hyaluronidase are dissolved at 4° C. in 5 liters of 0.1 M sodium acetate buffer (pH 6.0) which is 0.1 M with regard to sodium chloride. The addition is carried out slowly with gentle stirring, in order to avoid frothing. Ammonium sulphate is then added slowly, over the course of 3 hours, to give 50% saturation, 1450 g. ammonium sulphate being added, and the mixture stirred overnight. The suspension is centrifuged at 2,500 rpm for 1 hour and the precipitate is discarded. The supernatant is brought to 70% ammonium sulphate saturation by the careful addition of 700 g. of ammonium sulphate over the course of 2 to 3 hours, with continual stirring and then again stirred overnight, whereafter the solution is centrifuged at 2,500 rpm for 1 hour and the supernatant discarded. The precipitate may be stored at 4° C.

Stage 2

Ion Exchange Chromatography

The precipitate from Stage 1 is dissolved in about 300 ml. of 0.1 M phosphate buffer (pH 6.0) and transferred to a dialysis bag ($2\frac{3}{4}" \times 2'$). The volume of the bag should be sufficient to allow it to contain a final liquid volume of up to 1 liter. The contents are dialysed ($3 \times 24H$) against 0.1 M phosphate (pH 6.0) ($3 \times 5$ liters).

Half the enzyme solution is run on to an "Amberlite" CG50 column ($4.4 \times 30$ cm) at ambient temperature at a rate of 150 ml. per hour. The remainder of the solution may be kept in a plastics container for 24 hours at +4° C. before processing.

The column is washed with 1 liter or 0.1 M phosphate buffer (pH 6.0) at a rate of 200 ml. per hour. Excess buffer is removed from the top of the resin and the column is then eluted with 0.3 M phosphate (pH 8.5) at a rate of 100 ml. per hour. The initial 1.8 liters of 0.3 M phosphate (pH 8.5) eluated is collected, followed by the collection of 10 ml. fractions. Protein and enzyme activity are measured and the appropriate fractions pooled to give a maximum yield of enzyme with an overall minimum specific activity of 7,500 IU/mg.

The pool is dialysed against 70% saturated ammonium sulphate solution. The total liquid volume, internal and external to the dialysis bag, is adjusted to 2 liters and 900 g. ammonium sulphate are added to the system. Dialysis is continued at +4° C., at least overnight, while stirring, whereafter precipitated protein is spun down on a bench centrifuge. The precipitate may be stored at +4° C.

Stage 3

Gel Filtration

The precipitate from Stage 2 is dissolved in the minimum volume of 0.1 M sodium chloride solution (700 mg. protein should dissolve in 4 ml. of 0.1 M sodium chloride solution to give about 8 ml. total volume) and the enzyme solution applied to a column of "Sephadex" G75 superfine ($80 \times 4.4$ cm.) at a flow rate not exceeding 30 ml. per hour. 10 ml. fractions are collected, protein and enzyme activity are measured and the appropriate fractions pooled.

The pool is dialysed against 80% ammonium sulphate, 520 g. ammonium sulphate being added to 1 liter total volume, and stirred at least overnight at +4° C., whereafter the precipitate is isolated with a bench centrifuge and stored at +4° C.

The following Table 1 gives the normal range of results obtained when using the above-exemplified method:

TABLE 1

| Stage | Specific activity (IU/mg) | Protein mg. | Protein % | Enzyme Units total $\times 10^{-6}$ | % |
|---|---|---|---|---|---|
| crude enzyme | 300–450 | 125,000 | 100 | 38–500 | 100 |
| 50–70% ammonium sulphate cut | 1,100–1,700 | 20–30,000 | 16–24 | 32–40 | 70–80 |
| post "Amberlite" CG50 | 7,500–10,100 | 1700–2100 | 1.3–1.7 | 10–18 | 33–40 |
| post "Sephadex" G75 | 35–50,000 | 200–300 | 0.16–0.24 | 7–12 | 16–25 |

The following Table 2 gives the results obtained from one particular production run using the above-exemplified method:

TABLE 2

| | Main fraction | | | Side-fractions + discards | Total activity accounted for | |
|---|---|---|---|---|---|---|
| Stage | Total activity $\times 10^6$ IU | % Original activity | Specific activity (IU/mg) | Total activity ($10^6$ IU) | $\times 10^6$ IU | % Original activity |
| Crude enzyme | 49 | 100 | 436 | — | 49 | 100 |
| 50–70% Ammonium sulphate cut | 33 | 67 | 1,590 | 0–50% = 12 >70% = 0 | 45 | 92 |
| post "Amberlite" CG50 | (1) 8.4 (2) 8.5 } 17 | 35 | 8,390 | (1) 4.6 (2) 5.1 } 10 | 39 | 80 |
| post "Sephadex" G75 | (1) 6.3 (2) 4.7 } 11 | 22 | 40,400 | (1) 1.3 (2) 1.1 } 2.4 | 35 | 71 |

Polyacrylamide Gel Electrophoresis

Eight batches of the enzyme were studied using a Shandon analytical polyacrylamide gel electrophoresis apparatus at pH 8.3 (B.P.) and pH 4.3. Electrophoresis at pH 4.3 used a small pore 7.5% acrylamide gel and was carried out in accordance with the manufactures' instructions. Gels were loaded with the enzyme (10 to 50 μg.) in 10% sucrose and run towards the anode at 4 mA per gel for 90 minutes (pH 4.3) or until the bromophenol blue marker reached the bottom of the gels (pH 8.3). The gels were stained with either 1% naphthalene black in 7% acetic acid (pH 4.3) or 0.25% coomassie blue in water/methanol/acetic acid (227/227/46 v/v/v) (pH 8.3) and destained using an appropriate solvent.

The eight batches of enzyme all behaved similarly on electrophoresis. At pH 8.3, the enzyme (50 μg.) migrated 3-4 mm. into the gel as a single protein band. At pH 4.3, the enzyme (10-25 μg.) migrated 25-30 mm. into the gel as a single, slightly diffuse protein band. At pH 4.3, 50 g. of enzyme also showed a faint minor protein band which had migrated 13-15 mm. into the gel.

It is concluded that, under the above conditions of electrophoresis, the enzyme is largely homogeneous. The additional faint protein band which is only seen at pH 4.3 when a large amount of protein (50 μg.) is applied to the gel comprises only a small percentage of the total protein.

The following Table 3 gives the results of pH and light absorption measurments obtained with several batches of the new enzyme:

TABLE 3

| Batch No. | pH | Absorbance per 50,000 IU | |
|---|---|---|---|
| | | 280 nm | 260 nm |
| A | 5.0 | 0.52 | 0.30 |
| B | 5.1 | 0.58 | 0.34 |
| C | 5.2 | 0.55 | 0.33 |
| D | 5.2 | 0.49 | 0.29 |
| E | 5.3 | 0.46 | 0.28 |
| F | 5.2 | 0.54 | 0.33 |
| G | 5.1 | 0.60 | 0.365 |
| H | 5.35 | 0.53 | 0.32 |

The following Table 4 gives the results obtained from the measurement of the tyrosine content of several batches of the new enzyme:

TABLE 4

| Batch No. | % tyrosine per mg. protein (Lowry) | specific activity (IU/mg. tyrosine) |
|---|---|---|
| A | 8.1 | 631,000 |
| B | 8.8 | 612,000 |
| C | 6.6 | 690,000 |
| D | 8.1 | 631,000 |
| E | 7.6 | 658,000 |
| F | 7.8 | 595,000 |
| G | 8.2 | 595,000 |
| H | 7.4 | 595,000 |

The following Tables 5 and 6 show the average activities of other enzymes present in the crude starting material and in the enzyme according to the present invention:

TABLE 5

| | Units of enzyme activity per 100,000 IU of crude hyaluronidase and of the enzyme according to the present invention (number of analysis in brackets) | |
|---|---|---|
| | crude | new enzyme |
| Enzyme measured in purification pool | | |
| N—acetylhexosaminidase (μmoles min$^{-1}$) | 400-584(5) | 0.03-0.46(9) |
| Arylsulphatase A (μmoles min$^{-1}$) | 1.60-2.50(5) | 0.10-0.35(9) |
| Arylsulphatase B (μmoles min$^{-1}$) | 0.61-1.32(5) | 0.04-0.09(9) |
| Esterase (μmoles min$^{-1}$) | 2.1-6.6(5) | 0.01-0.02(9) |
| β-glucuronidase (μmoles min$^{-1}$ × 10$^3$) | 3-7(5) | not detected |
| Acid phosphatase (μmoles min$^{-1}$) | 7-21(3) | 0.10-0.32(5) |
| Acid protease (O.D. units min$^{-1}$) | 3.5-4.5(4) | 0.01(7) |
| Deoxyribonuclease (O.D. units min$^{-1}$) | 3.9-10.2(4) | 0.02-0.15(7) |
| Enzyme measured in dispensed freeze-dried new enzyme | | |
| N—acetyl hexosaminidase (μmoles min$^{-1}$) | | 0.02-0.22(8) |
| Arylsulphatase A (μmoles min$^{-1}$) | | 0.13-0.21(8) |
| Esterase (μmoles min$^{-1}$) | | 0.03-0.05(8) |

TABLE 6

| | enzyme units per 220,000 IU of activity of enzyme according to the present invention | |
|---|---|---|
| enzyme | enzyme according to the present invention | impure enzyme (420 IU mg$^{-1}$) |
| N—acetyl hexosaminidase$^{(a)}$ | 0.29 | 1192 |
| deoxyribonuclease$^{(b)}$ | 0.18 | 16.7 |
| acid phosphatase$^{(a)}$ | 0.46 | 26.4 |
| esterase$^{(a)}$ | 0.04 | 7.9 |
| acid protease$^{(b)}$ | 0.02 | 8.8 |
| arylsulphatase A$^{(a)}$ | 0.42 | 4.2 |
| arylsulphatase B$^{(a)}$ | 0.13 | 2.0 |
| β-glucuronidase$^{(a)}$ | 9 × 10$^{-5}$ | 1 × 10$^{-2}$ |

$^{(a)}$μmol product formed/min. per mg.
$^{(b)}$absorbance units/min. per mg.

The following Table 7 gives the bovine serum albumin content of randomly selected batches of the enzyme according to the present invention and of impure enzyme:

TABLE 7

| | μg. albumin per 220000 IU enzyme activity |
|---|---|
| batch | |
| A | 0.31 |
| B | 0.50 |
| C | 0.76 |
| D | 1.00 |
| E | 1.17 |
| F | 2.90 |
| G | 0.26 |
| impure enzyme | |
| A | 457 |
| B | 835 |

The following Table 8 gives the results of stability tests obtained by storing the enzyme in glass vials at 4° C. in the dark for varying periods:

TABLE 8

| batch | IU per vial before/after storage | storage period in months | % of original activity |
|---|---|---|---|
| A | 52000/55000 | 5 | 106 |
| B | 48600/30000 | 19 | 62 |
| C | 51600/45000 | 19 | 87 |
| D | 52100/50000 | 17 | 96 |
| E | 49000/60000 | 18.5 | 122 |
| F | 59400/61000 | 18.3 | 103 |
| G | 60000/47300 | 19.2 | 79 |
| H | 60000/50300 | 19 | 84 |
| I | 50000/48000 | 21.5 | 96 |
| J | 57000/51000 | 21.3 | 89 |
| K | 48000/51000 | 12.7 | 106 |

TABLE 8-continued

| batch | IU per vial before/after storage | storage period in months | % of original activity |
|---|---|---|---|
| L | 51000/46000 | 16.2 | 90 |
| M | 47500/48200 | 15.4 | 101 |
| N | 63000/59700 | 15.3 | 95 |
| O | 54500/45700 | 19.1 | 84 |
| P | 56300/46600 | 18.9 | 83 |
| Q | 65000/65000 | 14.9 | 100 |
| R | 59500/63500 | 12.0 | 107 |
| S | 55800/47500 | 12.4 | 85 |
| T | 54300/50800 | 12.2 | 94 |

CLINICAL STUDIES

Human Pharmacological and Safety Studies

Seven patients with suspected myocardial infarction were given the enzyme (200,000 IU) intravenously in open studies. The serum half life of the enzyme was determined and blood chemistry, haematology and ECG were monitored in these patients. Blood chemistry, haematology and ECG were also monitored as part of a double-blind trial and ECG was also done.

Serum half-life:

The enzyme activity disappeared rapidly from the serum, with half lives ranging from 2.5 to 5.7 minutes in the seven patients studied. The reason for this rapid clearance is not known but may be a result of the binding of the enzyme to tissue substrates.

Blood chemistry:

The enzyme produced no changes in creatine kinase (CK and its myocardial isoenzyme CKMB), hydroxybutyrate dehydrogenase (HBD), aspartate aminotransferase (AST), alanine aminotransferase (ALT), alkaline phosphatase (ALP), sodium, potassium, calcium, urea, creatinine, bilirubin, urate or total protein in the open study patients, although it was not possible to measure all analytes in all patients. Some analytes were outside the normal range as a result of the myocardial infarction but a comparison of the incidence of changes in CK, HBD, AST, ALT, Na, K, urea and creatinine in the double-blind study showed there was no difference in the incidence or severity of these changes in the enzyme and placebo groups.

Haematology:

In the open study the enzyme had no effect on haemoglobin (Hb), white blood cell count (WBC), red blood cell count (RBC), packed cell volume (PCV), differential count, platelets, erythrocyte sedimentation rate (ESR), thrombin time or prothrombin ratio, although it was not possible to measure all analytes in all patients. WBC and ESR were elevated in these patients but a comparison of the incidence and extent of these changes in the double-blind study showed there were no differences between the enzyme and placebo groups.

ECG data:

For technical and other reasons it was not possible to obtain suitable ECG data on the seven open study patients. However, ECG data from the double-blind studies showed that the enzyme significantly reduced Q wave development, maintained R waves and reduced the development of QRS abnormalities.

CLINICAL TRIALS

Protocols

Three double-blind studies have been carried out, all based on a similar protocol. The main provisions were:

(a) 200,000 units of the enzyme (potency $\geq 40,000$ units/mg) or placebo (normal saline) were given as a slow intravenous injection to patients with myocardial infarction within 6 hours of the onset of symptoms.

(b) All patients with typical symptoms were entered into the study and supportive evidence for the diagnosis of acute myocardial infarction in accordance with the WHO guidelines was obtained.

(c) Apart from the one enzyme/placebo injection, patients were treated in accordance with standard hospital practice.

(d) Patients were monitored up to hospital discharge and for up to 6 months.

(e) Patients were excluded from analysis if:
   (a) they were given the injection more than 6 hours after the onset of symptoms;
   (b) they were being treated with heparin, digoxin or antibiotics on admission;
   (c) they did not satisfy the WHO criteria of acute myocardial infarction.

Three studies were completed and the following deviations from this original design were found:

A. This study included 483 patients who presented with symptoms of myocardial infarction and they were given the enzyme/placebo in the casualty department.

B. This study was initially to include 60 to 80 acceptable patients as a pilot study but was extended and 193 patients were entered. Although all patients presenting at casualty department should have been entered, only those who survived after transfer to the coronary care unit were included as this was where the enzyme/placebo was administered. The physicians also decided to exclude any patients over 70 years old.

C. The proposed trial intake was 100 but only 79 patients were entered and 71 of these had confirmed infarction.

The main assessment of the effect of the enzyme was on patient mortality, which is a clear, definite end-point. Other assessments of the effects of the enzyme were by 35 lead ECG (Study C) or 12 lead ECG (Study B) and measurement of infarct size using CK isoenzymes and myocardial scanning (Study C).

Results:

A. All patients presenting at casualty department with suspected myocardial infarction were entered, including those in extremis with cardiogenic shock or unrecordable blood pressure.

483 patients (240 enzyme, 243 placebo) were entered. On an "intention to treat" basis, there was a statistically significant reduction in mortality in the enzyme-treated patients; overall, 72 patients died (27 enzyme (11%), 45 placebo (19%), $\chi^2 = 5.02$, $p < 0.05$). 128 patients (61 enzyme, 67 placebo) did not have a confirmed myocardial infarction. None of those patients who had the enzyme died and 5 patients from the placebo group died.

The results demonstrate that the enzyme is safe to use on an "intention to treat" basis and this is of considerable importance because in many cases treatment needs to be given before a diagnosis of myocardial infarction can be confirmed.

355 patients (179 enzyme, 176 placebo) had a confirmed myocardial infarction and 33 of these patients (13 enzyme, 20 placebo) breached the trial protocol requirements as they were receiving heparin, digoxin or antibiotics or received the trial material more than 6 hours after the onset of symptoms. However, these exclusions are not now considered necessary and all 355 patients with infarction are considered in the following results.

There was a considerable reduction in mortality in the enzyme-treated patients and overall 67 patients with infarction died (27 enzyme (15%); 40 placebo (23%), $\chi^2 = 3.39$, p <0.10). A "high risk" group of patients was identified (97 enzyme, 101 placebo) who had either systolic blood pressure <90 mm Hg and/or left ventricular failure and/or were aged over 65 years. 57 of these patients died (22 enzyme (23%), 35 placebo (35%); $\chi^2 3.45$, p <0.10).

11 "high risk" patients had an unrecordable blood pressure on admission to hospital (7 enzyme, 4 placebo) and these patients had an extremely poor prognosis. When these patients were excluded from the mortality analysis then mortality data for patients with myocardial infarction but with an initial recordable blood pressure, were:

| Group | Enzyme death/total (%) | Placebo death/total (%) |
|---|---|---|
| all patients | 21/172 (12%) | 37/172 (22%)* |
| high risk patients | 16/90 (18%) | 32/97 (33%)** |

*$\chi^2 = 5.3$, p < 0.025
**$\chi^2 = 5.66$, p < 0.02

Although a greater percentage of patients survived in the enzyme group than in the placebo group, the drugs prescribed on discharge from hospital and at 6 months were similar.

B. 193 patients (97 enzyme, 96 placebo) were entered. 18 patients (8 enzyme, 10 placebo) had not had a myocardial infarction, 39 patients (19 enzyme, 20 placebo) had a possible infarction or severe angina and 136 patients (70 enzyme, 66 placebo) had a confirmed infarction. 10 of these patients (5 in each group) were withdrawn as they breached the trial protocol. The pretreatment characteristics of the enzyme and placebo groups were similar. 13 patients with confirmed infarction died (5/56 enzyme (7.7%); 8/61 placebo (13.1%). This difference is not statistically significant due to the small number of patients but the results suggest that the enzyme has a clinically significant benefit. 4 patients with suspected infarction died (1/19 enzyme (5.3%); 3/20 placebo (15%)).

Analysis of the pre- and post-treatment electrocardiagrams showed that the enzyme treatment significantly reduced the extent of Q wave development and the development of abnormalities of the QRS complex. There was also some reduction in the loss of R waves but this did not reach statistical significance.

C. 79 patients (39 enzyme, 40 placebo) were entered. The enzyme group contained significantly more patients with cardiogenic shock, heart failure, peripheral hypoperfusion, pulmonary congestion and haemodynamic impairment than the placebo group at the time of admission to the study. 8 patients (4 enzyme, 4 placebo) were found not to have had a myocardial infarction. 7 patients died in hospital, 5 in the enzyme group and 2 given placebo. 4 of the 5 deaths in the enzyme group were in the "high risk" category, the 2 deaths in the placebo group were in the lower risk patients.

Analysis of 35 lead ECG data from "vulnerable" leads (each patient acting as their own control) showed that Q wave development and R wave loss between days 1 and 3 post infarction were significantly reduced in the enzyme-treated patients compared to patients given placebo.

Adverse Reactions

The only adverse reactions reported were one case of rash which cleared within 3 days and 10 patients having brief episodes of rigors or shivering between 0.5 and 2 hours after injection. In the former case, the patient was receiving other drugs (lorazepam and cyclizine) and in the latter cases it is thought that this reaction may have been due to the method and speed of injection.

Discussion

Myocardial infarction is a serious disease which, particularly in the elderly patient with complications, such as pulmonary oedema and venous congestion, can be fatal. In the years 1977–1979, the number of deaths due to acute myocardial infarction (OPCS Mortality Statistics) was well over 100,000 per annum. It is impossible to correlate these figures with the present studies, which covered only patients admitted to hospital and where patients were followed for a maximum of 6 months. However, even a reduction of one percent in the annual mortality rate would save over 1000 lives.

Study A was designed and carried out to represent as closely as possible the normal intake and treatment of patients with suspected myocardial infarction. Confirmation of this was obtained by establishing that the percentage of deaths in hospital for the placebo group was close to the previous in-hospital death rate. Under these conditions, for all patients entered on an "intention to treat" basis, the death rate at 6 months was reduced from 19% in the placebo group to 11% in the enzyme-treated group. In patients with confirmed infarction, 23% died in the placebo group, compared with 15% in patients given the enzyme. This reduction of the mortality rate of some 35% could result in the saving of many thousands of lives if the enzyme were to be in general use.

The other two studies included smaller numbers of patients and in one (Study C) the patient pretreatment characteristics in the placebo and the enzyme groups were significantly different. In the other study (Study B), the mortality rate at 4 months in the placebo group was 13.0% and in the enzyme group was 7.7%. Both these figures are much lower than those in Study A but they also show a 41% reduction in mortality at 4 months by the use of the enzyme.

Confirmatory evidence of the benefit of the enzyme on the myocardium was seen in both these latter two studies by examination of the pre- and post-injection electrocardiograms.

Conclusions

The enzyme according to the present invention, given as a single intravenous injection, has been shown to be safe and well tolerated when given to patients presenting with suspected myocardial infarction. On an "intention to treat" basis and in patients with confirmed myocardial infarction, particularly those at high risk, there was a significant reduction in mortality in patients treated with the enzyme when compared with patients given placebo.

The enzyme according to the present invention is preferably in lyophilised form in a vial containing approximately 220,000 IU of enzyme activity, the unit dose being 200,000 IU. The average of 20,000 IU is intended to cover losses during injection. Each vial preferably also contains 150 to 350 µg. of sodium acetate B.P. The vials should be stored in a dry place at about 4° C.

In order to use the enzyme, the contents of a vial are dissolved in 2.2 ml. of sodium chloride intravenous infusion B.P., without shaking. The solution is drawn up slowly into a plastics syringe and 2.0 ml. injected intravenously at a slow and constant rate.

We claim:

1. An enzyme which is an odorless, white powder, the pH of a 15000 to 22000 IU/ml. solution of which is carbon dioxide-free physiological saline solution suitable for injection is 4.5 to 7.5, the solution being clear and colorless; a solution of 50000 IU of which in 3 ml. carbon dioxide-free physiological saline solution suitable for injection has a light absorption of not more than 0.60 at 280 nm and of not more than 0.37 at 260 nm; the enzyme having the following percentage amino acid analysis:

| | | |
|---|---|---|
| Asp 11.1 ± 0.4; | Thr 5.8 ± 0.1; | Ser 6.4 ± 0.2; |
| Glu 9.1 ± 0.2; | Pro 5.0 + 0.5; | Gly 6.6 ± 0.2; |
| Ala 7.4 ± 0.1; | Val 7.9 + 0.5; | Met 0.8 ± 0.1; |
| Ile 5.2 ± 0.2; | Leu 10.9 + 0.2; | Tyr 4.4 ± 0.1; |
| Phe 4.5 ± 0.1; | His 2.8 + 0.2; | Lys 7.6 ± 0.4; |
| Arg 5.6 ± 0.1; | | | said enzyme having a total hexose content of 10.6+0.003%; said enzyme containing not more than 5 µg. albumin per 220000 KU of activity, said enzyme having a molecular weight of 62000 to 70000 determined by gel infiltration and said enzyme having a specific activity of at least 35000 IU/mg.

2. The enzyme according to claim 1, produced by a process which comprises:
subjecting crude hyaluronidase to an ammonium sulphate fractionation by adding ammonium sulphate to a buffered solution of crude hyaluronidase until the degree of ammonium sulphate saturation is about 50%, the precipitate obtained being discarded and the supernatant being adjusted to 70% ammonium sulphate saturation, the precipitate obtained being dialyzed and then applied to a cross-linked polyacrylic divinylbenzene resin, whereafter the resin is first washed with 0.1 M phosphate buffer and subsequently eluted with 0.3 M phosphate buffer, the eluate then being subjected to gel filtration through a cross-linked dextran gel which does not contain active carboxymethyl groups followed by isolation of the enzyme.

3. The enzyme according to claim 2, wherein the precipitate obtained by the ammonium sulphate fractionation is separated by centrifuging.

4. The enzyme according to claim 2, wherein the precipitate to be dialysed is dissolved in 0.1 M phosphate buffer (pH 6.0) and dialysed against the same buffer.

5. The enzyme according to claim 2, wherein the 0.1 M phosphate buffer used for washing the resin has a pH of 6.0.

6. The enzyme according to claim 2, wherein the 0.3 M phosphate buffer used for eluting the resin has a pH of 8.5.

7. A dosage unit form comprising approximately 220000 IU of the enzyme according to claim 1 in lyophilized form.

8. A dosage unit form according to claim 7, which additionally contains 150 to 350 µg. sodium acetate.

9. A method of treating a patient for myocardial infarction, which comprises injecting into the circulatory system of such a patient the enzyme according to claim 1 in an amount effective to bring about alleviation of the symptoms of myocardial infarction.

* * * * *